(12) United States Patent
Gärber et al.

(10) Patent No.: US 7,584,752 B2
(45) Date of Patent: Sep. 8, 2009

(54) DEVICE AND PROCESS FOR CONTROLLING A RESPIRATOR

(75) Inventors: Yvo Gärber, Lübeck (DE); Hans Matthiessen, Bad Schwartau (DE); Dieter Weismann, Gross Grönau (DE); Eckhard Teschner, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 611 days.

(21) Appl. No.: 11/277,270

(22) Filed: Mar. 23, 2006

(65) Prior Publication Data

US 2006/0260611 A1    Nov. 23, 2006

(30) Foreign Application Priority Data

May 18, 2005    (DE) ........................ 10 2005 022 896

(51) Int. Cl.
*A61M 15/00* (2006.01)
(52) U.S. Cl. ................................................. 128/204.23
(58) Field of Classification Search ............ 128/204.23, 128/204.18, 203.12; 600/529, 533

See application file for complete search history.

(56) References Cited

U.S. PATENT DOCUMENTS 7,162,296 B2 * 1/2007 Leonhardt et al. ........... 600/547

FOREIGN PATENT DOCUMENTS

DE         103 01 202 B3    1/2004
EP          0 791 327 A2    8/1997

OTHER PUBLICATIONS

Adler, et al., "Monitoring of Lung Volume in Dogs with Electrical Impedance Tomography", 1996, 18th Annual International Conference of the IEEE Engineering in Medicine and Biology Society, p. 776-777.*

* cited by examiner

*Primary Examiner*—Steven O Douglas
(74) *Attorney, Agent, or Firm*—McGlew and Tuttle, P.C.

(57) ABSTRACT

A device and a process for determining the change in the functional residual capacity (FRC) in a simple manner. Based on a first respiration phase for mechanical respiration, a recruitment maneuver is performed for this during a second respiration phase, and respiration is switched back to mechanical respiration during a third respiration phase. Reference values $U_{ref1}$, $U_{ref3}$ are formed from the end-expiratory values of the impedance measured signals U during the first respiration phase and the third respiration phase, and the difference $\Delta U$ ($\Delta FRC$) between the reference value $U_{ref3}$ of the third respiration phase and the reference value $U_{ref1}$ of the first respiration phase is an indicator of the change in the functional residual capacity of the lung of the test subject.

8 Claims, 3 Drawing Sheets

DEVICE AND PROCESS FOR CONTROLLING A RESPIRATOR

CROSS REFERENCE TO RELATED APPLICATIONS

This application claims the benefit of priority under 35 U.S.C. § 119 of German Patent Application DE 10 2005 022 896.8 filed May 18, 2005, the entire contents of which are incorporated herein by reference.

FIELD OF THE INVENTION

The present invention pertains to a device and a process for controlling a respirator (ventilator).

BACKGROUND OF THE INVENTION

Electroimpedance tomography (EIT) is a method in which a weak electric alternating current is fed into the human body in order to measure the surface potentials at different points of the body. By rotating the points at which the current is fed into the body while measuring the surface potentials at the same time, it is possible to determine a two-dimensional tomogram of the electric impedance distribution in the body being examined by means of suitable mathematical reconstruction algorithms. In medicine, a tomogram of the impedance distribution of the human body is of interest because the electric impedance changes both with the air content and the extracellular fluid content in the tissue. The ventilation of the lung as well as the shifts in blood and serum parameters can thus be visualized and monitored in a regionally resolved manner.

To carry out gentle respiration of the patient, it is necessary to know the functional residual capacity (FRC) of the subject's lung. The functional residual capacity is defined as the volume of gas that remains in the lung at the end of expiration. If, for example, a plurality of alveoli are collapsed, the FRC is smaller than when the alveoli are open. A frequently used method for measuring the FRC according to the so-called wash-in or wash-out method is described, for example, in EP 791 327 A1. This measurement can be carried out during mechanical respiration.

The combination of a respiration system with a measuring system for electric impedance tomography is described in DE 103 01 202 B3. The measurements at the test subject can be carried out at exactly defined points in time and as a function of the course of respiration due to the bidirectional data exchange between the respiration system and the measuring system for electric impedance tomography.

If, for example, a respiration maneuver is initiated in a patient in the form of a brief pressure rise (recruitment maneuver) as a possible method for improving ventilation, a plurality of variables should change in the successful case. Thus, an attempt is made by means of the recruitment maneuver to reinflate collapsed regions of the lungs, so that these regions will again participate in the ventilation and gas exchange will thus improve. Both the ventilation and the FRC will improve in case of a successful recruitment maneuver without already ventilated regions being compromised by the brief pressure rise. However, information on the FRC and the change in the FRC is usually unavailable. It is of little benefit if a majority of the increase in the FRC and/or of the improvement of ventilation increases in regions that were already well ventilated before the recruitment maneuver and the actually collapsed target regions hardly benefit or benefit only little from the inflating. Consequently, it is of fundamental interest for the user to know which region of the lung has contributed to the change in ventilation and FRC. The breakdown of the FRC or the change in FRC and ventilation or change in ventilation according to local contributions of various regions of the lungs is called the regional or even local FRC or FRC change and regional or local ventilation or ventilation change in this connection. This is to be understood in the sense of characteristic values within ROIs (Region of Interest). It can be assumed that it is possible to determine the regional ventilation or ventilation change by means of electroimpedance tomography. A local FRC determination or FRC change can be estimated so far only by computed tomography and partly also by X-ray, with the known disadvantageous effects of these methods on the patient. Besides the recruitment maneuver, an FRC change can also be obtained from the administration of a drug or from the recovery of the lung.

SUMMARY OF THE INVENTION

The basic object of the present invention is to propose a device and a process for determining the change in the functional residual capacity (FRC) in a simple manner.

According to the invention, a process is provided for controlling a respirator in combination with a electroimpedance measuring device, which receives impedance measured signals U via a electrode application arranged on the upper body of a test subject. The process includes setting a mode for pressure-controlled or volume-controlled, mechanical respiration on the respirator during a first respiration phase. A first reference value $U_{ref1}$ is calculated from the obtained end-expiratory values of the impedance measured signals U, which values are correlated with the respiration cycle. A second reference value $U_{ref3}$ is formed from the end-expiratory values of the impedance measured signals U during another respiration phase during mechanical respiration. A difference is formed from the second reference value $U_{ref3}$ and the first reference value $U_{ref1}$ and is taken as an indicator of a change in the functional residual capacity (FRC) of the lung of the test subject (3).

According to another aspect of the invention, a respirator (ventilator) combined with an electroimpedance measuring device is provided. The combination includes an electrode application, which is arranged on the upper body of a test subject and detects impedance measured signals U. A control electronic unit is provided at the respirator for setting phases of respiration for pressure- or volume-controlled mechanical respiration. An evaluating unit is provided which calculates a first reference value $U_{ref1}$ from the end-expiratory values of the impedance measured signals U during a first respiration phase and forms a second reference value $U_{ref3}$ from the end-expiratory values of the impedance measured signals U during another respiration phase during mechanical respiration. The difference between the second reference value $U_{ref3}$ and the first reference value $U_{ref1}$ is an indicator of the change in the functional residual capacity (FRC) of the lung of the test subject.

The advantage of the present invention is essentially that a first reference value is formed from end-expiratory values of the impedance measured signals during a first phase of respiration for mechanical respiration. During the later phase of respiration, a second reference value is formed from the end-expiratory values of the impedance measured signals during mechanical respiration. The change in the functional residual capacity (FRC) of the test subject's lung is determined by comparing the reference values from the phases of respiration investigated. A noninvasive measurement method, which is not stressful for the test subject, and with which the local change in the lung volume can be determined, is available in electroimpedance tomography.

The relative change in impedance $\Delta Z/Z_{ref}$ is obtained in impedance tomography from the relative voltage changes $\Delta U/U_{ref}$ on the body surface of the test subject, which develop during the different current feeds.

There is an alternation of inspiration and expiration during mechanical respiration, the change in impedance, $\Delta Z$, therefore varies between an end-inspiratory value and an end-expiratory value.

The relationship between $\Delta Z$ and $\Delta U$ is given, in a linear approximation, by $$\frac{\Delta Z^i}{Z^i_{ref}} = \sum_{\mu=1}^{M} b_{i\mu} \frac{\Delta U^\mu}{U^\mu_{ref}},$$

in which $\mu=1, \ldots M$ represent the measured indices that characterize the power feed and voltage measurement positions, $U_{ref}$ is the end-expiratory reference voltage and $\Delta U$ is the difference between the end-inspiratory voltage and the end-expiratory reference voltage (for all values of $\mu$). The $b_{i\mu}$ values are the coefficients of the reconstruction matrix (e.g., filtered back-projection).

Furthermore, it is assumed that the relative change in impedance $\Delta Z/Z_{ref}$ is proportional to the tidal volume $V_T$.

$$V_T = c_V \sum_{i=1}^{n} \frac{\Delta Z^i}{Z^i_{ref}},$$

in which the sum runs over all N pixels of the image, $Z_{ref}$ is the end-expiratory reference impedance distribution here (in the sense of the N image pixels) and $\Delta Z$ is the difference between the end-inspiratory and end-expiratory impedance distributions, and $c_v$ is the proportionality factor between the relative change in impedance and the tidal volume, which is called the volume factor here.

An exemplary embodiment of the present invention is shown in the figure and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
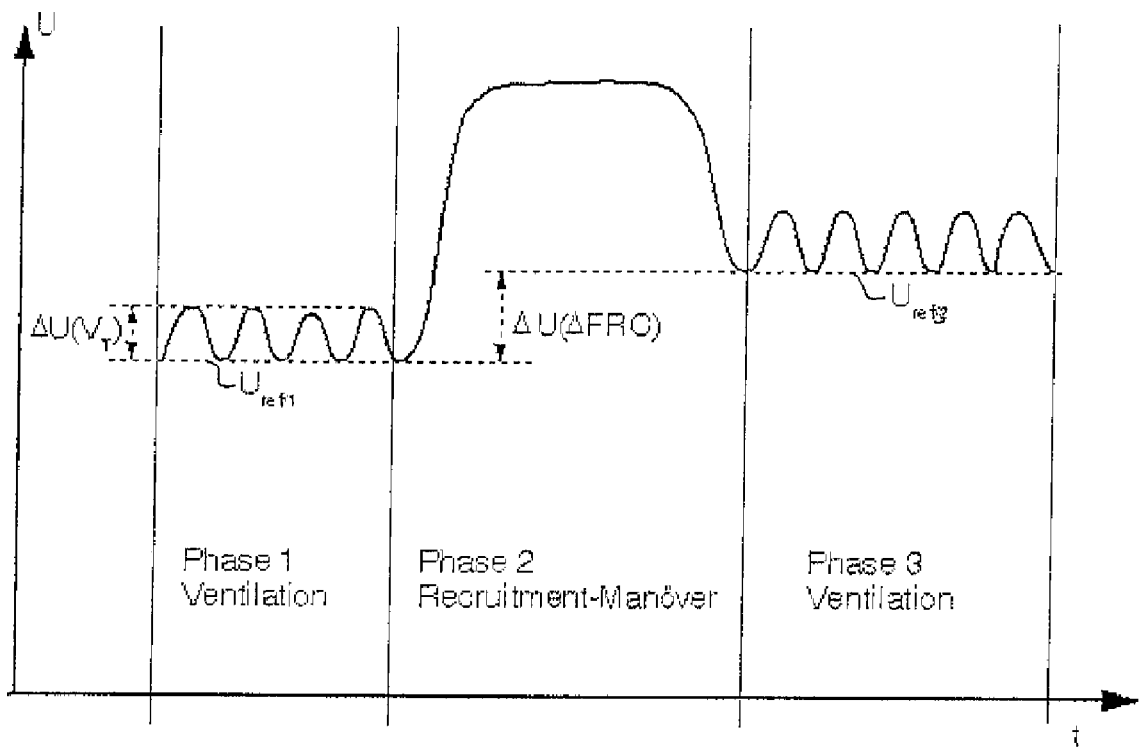
FIG. 1 is a diagram showing the course of the electroimpedance measured signals during different phases of respiration.

Referring to the drawings in particular, FIG. 1 schematically illustrates the course of impedance measured signals U during the alternation of mechanical respiration, respiration phase 1, at the time of a recruitment maneuver, respiration phase 2, and back to mechanical respiration, respiration phase 3.

An electroimpedance measurement is carried out during respiration phase 1 during as uniform respiration as possible. Since the tidal volume $V_T$ is known from the respirator, this can be used to determine the volume factor $c_v$ during respiration phase 1. After the end of the recruitment maneuver during respiration phase 2, the electroimpedance measurement is continued in respiration phase 3 in order to find possible differences in local ventilation compared to respiration phase 1.

At least two ranges, within which at least two end-expiratory reference voltages $U_{ref}$ are determined and are used to determine the local change in FRC, are marked during the electroimpedance measurement. One of the ranges is in respiration phase 1, the other in respiration phase 3.

The reference voltages $U_{ref}$ can be determined, e.g., such that the minimal voltages of each measuring position $\mu$ are determined within the fixed ranges for each breath. By coupling the electroimpedance measuring system with the respirator, the electroimpedance measuring device is triggered for measuring end-expiratory reference voltages. The end-expiratory reference voltages $U_{ref}$ thus determined can be averaged within the ranges, so that a data set of end-expiratory reference voltages $U_{ref1}$, $U_{ref3}$ are obtained for each range. Respiration phase 1 and respiration phase 3 are selected as ranges of interest in FIG. 1 in order to determine the local change in FRC. The corresponding relative change in impedance is determined from the relative difference of the end-expiratory reference voltages $U_{ref1}$ of respiration phase 1 and $U_{ref3}$ of respiration phase 3 according to $$\frac{Z^i_{ref/3} - Z^i_{ref/1}}{Z^i_{ref/1}} = \sum_{\mu=1}^{M} b_{i\mu} \frac{U^\mu_{ref/3} - U^\mu_{ref/1}}{U^\mu_{ref/1}}$$

It is assumed that the change in the reference voltages $U_{ref3}$ minus $U_{ref1}$ from respiration phase 1 to phase 3 following the application of the recruitment maneuver in phase 2 is caused by the change in the conductivity distribution because of the change in FRC. Since the relative change in conductivity from respiration phase 1 to respiration phase 3 can be locally reconstructed from the corresponding relative voltage differences, we gain access to the distribution of the FRC change within the regions of the lungs. Based on the presumed proportionality between the relative change in impedance and the change in the amount of air in the lung, the volume factor $c_v$ of the local ventilation, which was determined from respiration phase 1 concerning the reference conductivity distribution $Z_{ref1}$, can be used to obtain an estimate of the local change in FRC (pixel number I) for the target set. The change in FRC, $\Delta FRC$, is obtained as:

$$\Delta FRC^i = c^i_V \frac{Z^i_{ref/3} - Z^i_{ref/1}}{Z^i_{ref/1}}$$

$$= c^i_V \sum_{\mu=1}^{M} b_{i\mu} \frac{U^\mu_{ref/3} - U^\mu_{ref/1}}{U^\mu_{ref/1}}$$

Figure 2:
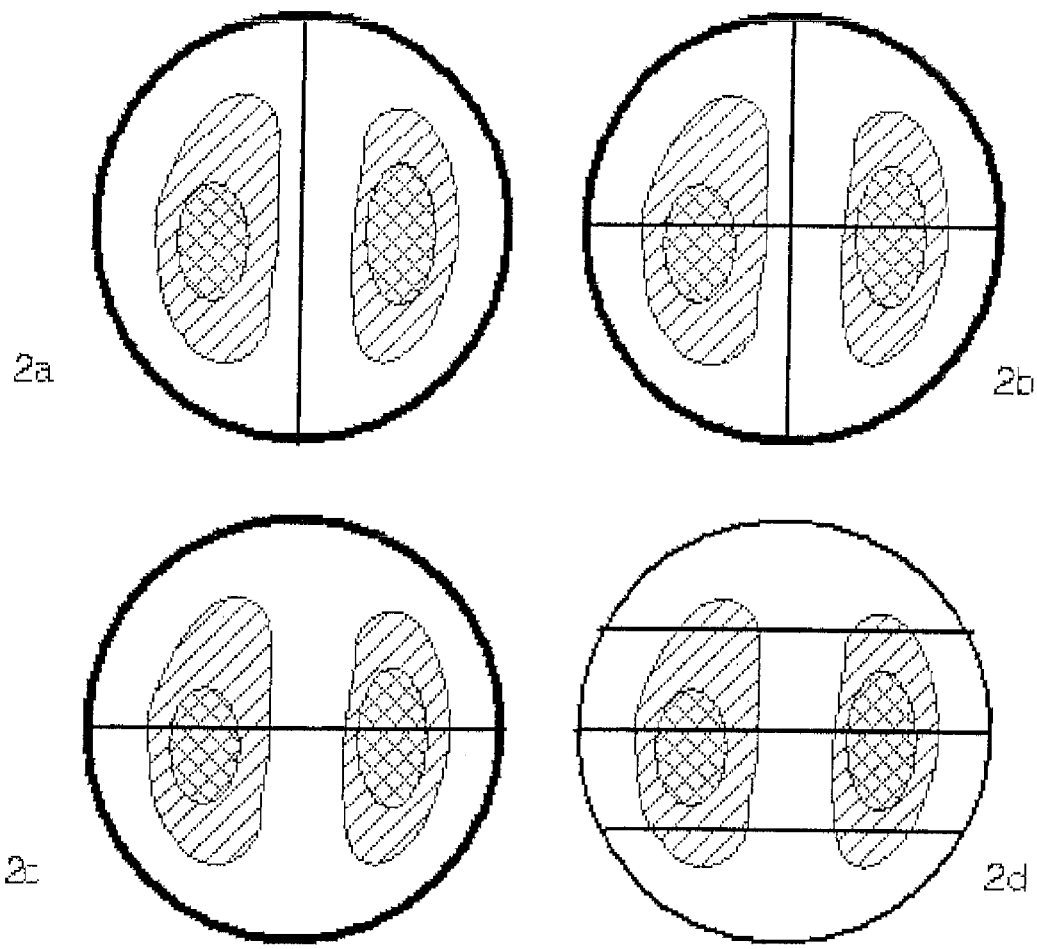
FIG. 2a is a view showing the breakdown of the computerized evaluation of electroimpedance measured signals in ROIs.
FIG. 2b is a view showing the breakdown of the computerized evaluation of electroimpedance measured signals in ROIs.
FIG. 2c is a view showing the breakdown of the computerized evaluation of electroimpedance measured signals in ROIs.
FIG. 2d is a view showing the breakdown of the computerized evaluation of electroimpedance measured signals in ROIs.

The local change in FRC is summed up graphically or numerically and represented within the ROIs. Such a breakdown of a computerized evaluation into ROIs is illustrated as an example in FIG. 2 and is described in US journal: Victorino, J. A. et al., Imbalances in Regional Lung Ventilation, *Am. J Respir. Crit. Care Med.*, Vol. 169 (2004), pp. 791-800.

The entire range is divided into a right-hand range and a left-hand range, corresponding to FIG. 2*a*, or a breakdown into four quadrants is performed corresponding to FIG. 2*b*. The entire range may also be decomposed into or four horizonl segments, corresponding to FIG. 2*c* or FIG. 2*d*.

Figure 3:
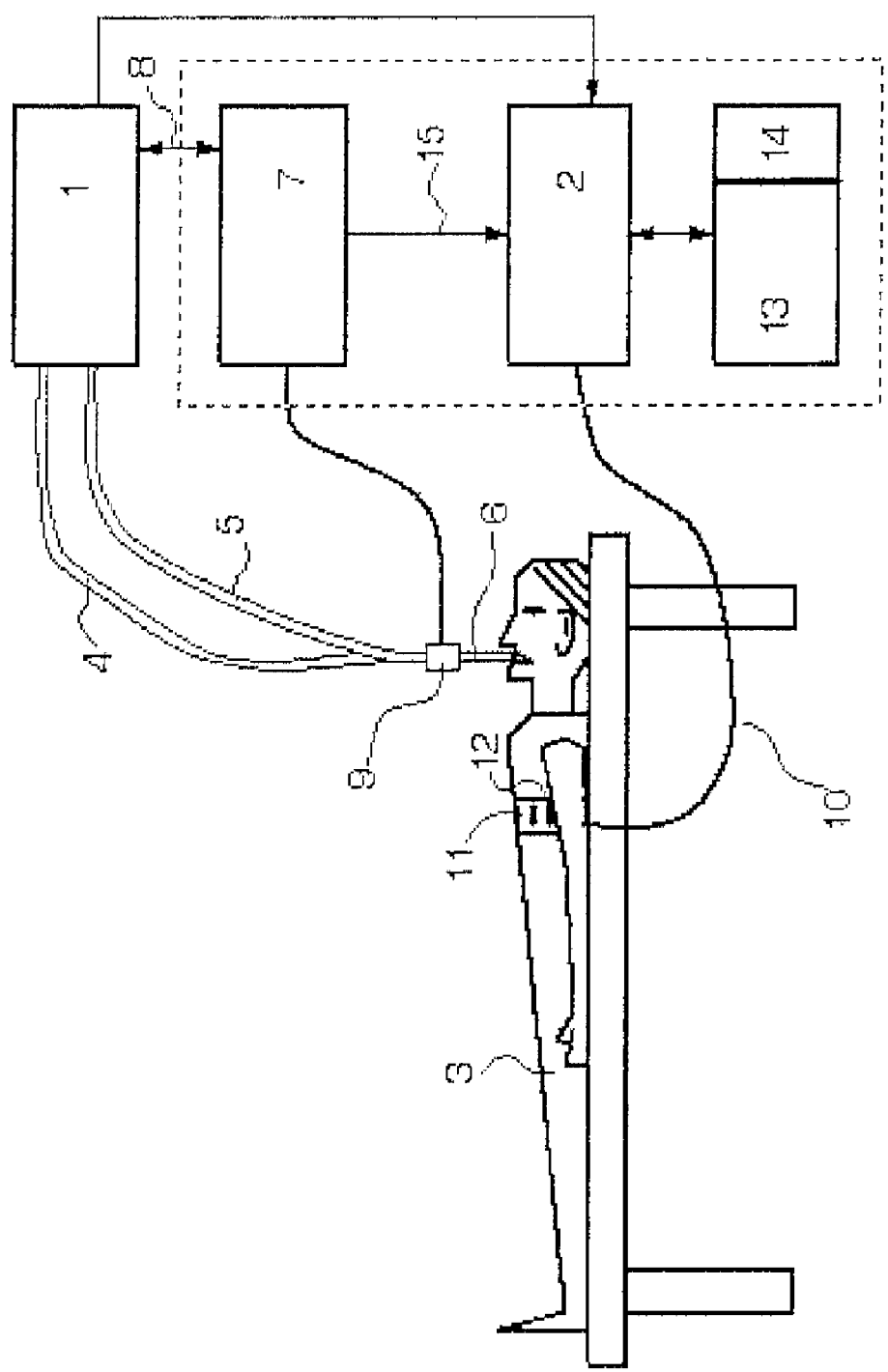
FIG. 3 is a schematic view showing the combination of a respirator with an electroimpedance measuring device to determine electroimpedance measured signals.

FIG. 3 schematically illustrates the structure of an electroimpedance measuring device 2 connected to a respirator (ventilator) 1 for determining the change in the functional residual capacity (FRC) of the lung of a test subject (3). The respirator 1 is connected with the lungs of the test subject 3 via an inspiration line 4 and an expiration line 5 as well as a tube 6. Different respiration phases are set from a control and measuring electronic unit 7. The control and measuring electronic unit 7 is connected for this to the respirator 1 via a bidirectional data line 8. A flow sensor 9 is connected to the tube 6 and supplies measured flow values to the control and measuring electronic unit 7 during the phases of respiration. The electroimpedance measuring device 2 is connected to an electrode belt 11 laid around the upper body of the test subject 3 via a data line 10. The electrodes 12 of the electrode belt 11 supply impedance measured values U. An evaluating unit 13 calculates data sets, which are displayed on a display unit 14, from the impedance measured signals. Via a trigger line 15, the electroimpedance measuring device 2 receives switching signals for switching between inspiration phase and expiration phase of the respirator 1. These switching signals are needed as trigger signals to determine relative minima or relative maxima of the impedance measured signals U.

While a specific embodiment of the invention has been shown and described in detail to illustrate the application of the principles of the invention, it will be understood that the invention may be embodied otherwise without departing from such principles.

What is claimed is:

1. A process for controlling a respirator in combination with an electroimpedance measuring device, which receives impedance measured signals U via an electrode application arranged on the upper body of a test subject, the process comprising the steps of:
    setting a mode for pressure-controlled or volume-controlled, mechanical respiration on the respirator during a first respiration phase;
    obtaining end-expiratory values of said impedance measured signals U during one respiration phase of a respiration cycle of mechanical respiration, said values being correlated with the respiration cycle;
    calculating a first reference value $U_{ref1}$ from the obtained end-expiratory values of the impedance measured signals U;
    obtaining other end-expiratory values of said impedance measured signals U during another respiration phase during mechanical respiration;
    forming a second reference value $U_{ref3}$ from the other end-expiratory values of said impedance measured signals; and
    forming a difference from the second reference value $U_{ref3}$ and the first reference value $U_{ref1}$ to provide an indicator of a change in the functional residual capacity (FRC) of a lung of the test subject.

2. A process in accordance with claim 1, wherein said first reference value and second reference value are formed as a mean value from the end-expiratory values of the impedance measured signals U.

3. A process in accordance with claim 1, wherein said end-expiratory values are determined by a trigger signal sent by the respirator.

4. A respirator and electroimpedance measuring device combination, comprising:
    an electrode application arranged on an upper body of a test subject to detect impedance measured signals U;
    a control electronic unit at the respirator for setting phases of respiration for pressure controlled mechanical respiration or volume-controlled mechanical respiration;
    an evaluating unit, which calculates a first reference value $U_{ref1}$ from end-expiratory values of the impedance measured signals U during a first respiration phase during mechanical respiration, forms a second reference value $U_{ref3}$ from the end-expiratory values of the impedance measured signals U during another respiration phase during mechanical respiration, and determines a functional residual lung capacity of a test subject based on a difference between the second reference value $U_{ref3}$ and the first reference value $U_{ref1}$.

5. A combination in accordance with claim 4, further comprising a trigger line provided between the respirator and the electroimpedance measuring device for transmitting trigger signals correlated with a respiration cycle.

6. A process for controlling a respirator, the process comprising:
    providing a respirator;
    providing an electroimpedance measuring device comprising an electrode application;
    arranging said electrode application on an upper body area of a test subject, said electroimpedance measuring device receiving impedance measured signals U via said electrode application;
    setting a mode for pressure-controlled or volume-controlled, mechanical respiration on said respirator during a first respiration phase;
    determining first end-expiratory values of said impedance measured signals U during one respiration phase of a respiration cycle of said respirator during mechanical respiration, said values being correlated with the respiration cycle;
    calculating a first reference value $U_{ref1}$ from said first end-expiratory values of the impedance measured signals U;
    determining second end-expiratory values of said impedance measured signals U during a second respiration phase during mechanical respiration;
    forming a second reference value $U_{ref3}$ from said second end-expiratory values of said impedance measured signals U; and
    determining an indicator of a local change in functional residual lung capacity in one or more areas of the lung of a test subject based on a difference from said second reference value $U_{ref3}$ and said first reference value $U_{ref1}$.

7. A process in accordance with claim 6, wherein said first reference value and second reference value are formed as a mean value from said first and said second end-expiratory values of the impedance measured signals U.

8. A process in accordance with claim 6, wherein said first end-expiratory values and said second end-expiratory values are determined by a trigger signal sent by the respirator.

* * * * *